(12) United States Patent
Eckstein et al.

(10) Patent No.: US 9,586,000 B2
(45) Date of Patent: Mar. 7, 2017

(54) CONNECTION DEVICE FOR USE IN THE NEGATIVE PRESSURE TREATMENT OF WOUNDS

(71) Applicant: PAUL HARTMANN AG, Heidenheim (DE)

(72) Inventors: Axel Eckstein, Heidenheim (DE); Pierre Croizat, Herbrechtingen (DE); Ali Sagas, Kfar-Kama (IL); Oded Stein, Kfar-Kama (IL)

(73) Assignee: PAUL HARTMANN AG, Heidenheim (DE)

( * ) Notice: Subject to any disclaimer, the term of this patent is extended or adjusted under 35 U.S.C. 154(b) by 801 days.

(21) Appl. No.: 13/962,713

(22) Filed: Aug. 8, 2013

(65) Prior Publication Data

US 2014/0046281 A1 Feb. 13, 2014

Related U.S. Application Data

(60) Provisional application No. 61/681,371, filed on Aug. 9, 2012.

(30) Foreign Application Priority Data

Aug. 9, 2012 (DE) .......................... 10 2012 214 178

(51) Int. Cl.
*A61M 1/00* (2006.01)
*A61M 3/02* (2006.01)
(52) U.S. Cl.
CPC ........ *A61M 3/0279* (2013.01); *A61M 1/0039* (2013.01); *A61M 1/0088* (2013.01)

(58) Field of Classification Search
CPC .............. A61M 1/0088; A61M 1/0039; A61M 1/0058; A61M 27/00; A61M 3/0279
See application file for complete search history.

(56) References Cited

U.S. PATENT DOCUMENTS 5,636,643 A * 6/1997 Argenta .................. A61F 13/02
128/897
5,836,311 A 11/1998 Borst et al.
(Continued)

FOREIGN PATENT DOCUMENTS

DE 102010006272 7/1928
DE 69628341 3/2004
(Continued)

*Primary Examiner* — Philip R Wiest
*Assistant Examiner* — Ariana Zimbouski
(74) *Attorney, Agent, or Firm* — Henry M. Feiereisen LLC (57) ABSTRACT

A connection device for use in the negative pressure therapy of wounds includes a flexible conduit which can be impinged with negative pressure and/or fluid media, the conduit having at least two lumens, a coupling body formed by an elastomeric flexible material which is non-detachably injection molded to a wound-side end section of the conduit, and being constructed for placement on a negative pressure bandage which covers and seals the wound negative pressure tight against the atmosphere, the conduit communicating through at least one opening in the coupling body with the wound space, and an end cap attached and preferably non-detachably fastened to the injection molded-on material of the coupling body, thereby sealing the coupling body tight against the outside.

25 Claims, 5 Drawing Sheets

(56) References Cited

U.S. PATENT DOCUMENTS

| | | | |
|---|---|---|---|
| 6,211,426 B1* | 4/2001 | Abrams | A61F 13/0203 128/888 |
| 6,572,945 B2* | 6/2003 | Bries | C09J 7/02 24/306 |
| 7,320,594 B1* | 1/2008 | Rizoiu | A61B 18/201 433/29 |
| 8,246,591 B2* | 8/2012 | Braga | A61M 1/0088 604/119 |
| 2001/0031943 A1* | 10/2001 | Urie | A61M 1/0088 604/43 |
| 2006/0100586 A1 | 5/2006 | Karpowicz et al. | |
| 2010/0063464 A1 | 3/2010 | Meyer et al. | |
| 2010/0137775 A1* | 6/2010 | Hu | A61M 1/0088 602/54 |
| 2011/0028917 A1* | 2/2011 | Hall | A61M 1/0058 604/290 |
| 2011/0077605 A1* | 3/2011 | Karpowicz | A61M 1/0001 604/318 |
| 2011/0152800 A1 | 6/2011 | Eckstein et al. | |
| 2011/0184361 A1 | 7/2011 | Crojzat et al. | |
| 2011/0184362 A1 | 7/2011 | Croizat et al. | |
| 2011/0282309 A1* | 11/2011 | Adie | A61M 1/0088 604/319 |
| 2012/0184931 A1 | 7/2012 | Horn et al. | |
| 2012/0226247 A1 | 9/2012 | Danei et al. | |
| 2013/0030395 A1 | 1/2013 | Croizat et al. | |

FOREIGN PATENT DOCUMENTS

| | | |
|---|---|---|
| DE | 202011109057 | 3/2011 |
| DE | 102009060596 | 6/2011 |
| DE | 102010006273 | 7/2011 |
| DE | 2011009241 | 7/2012 |
| DE | 102011108726 | 1/2013 |
| EP | 1 129 734 A2 | 9/2001 |
| EP | 2495009 | 9/2012 |
| WO | WO2009/124548 | 10/2009 |

* cited by examiner

CONNECTION DEVICE FOR USE IN THE NEGATIVE PRESSURE TREATMENT OF WOUNDS

CROSS-REFERENCES TO RELATED APPLICATIONS

This application claims the benefit of prior filed U.S. provisional Application No. 61/681,371, filed Aug. 9, 2012, and of German Patent Application, Serial No. 10 2012 214 178.2, filed Aug. 9, 2012, pursuant to 35 U.S.C. 119(e), the disclosure of which is incorporated herein by reference.

BACKGROUND OF THE INVENTION

The invention relates to connection device for use in the negative pressure treatment of wounds.

The following discussion of related art is provided to assist the reader in understanding the advantages of the invention, and is not to be construed as an admission that this related art is prior art to this invention.

In the recent past, the negative pressure treatment of wounds, in particular of problematically healing wounds, has gained increasing importance. Negative pressure treatment means that a body or wound area which is exposed to the surrounding atmosphere is sealed against the environment i.e., the atmosphere in which we live and breathe, pressure tight or negative pressure tight, wherein within the sealed wound region a pressure which is lower relative to the atmospheric pressure, i.e., a negative pressure can be applied and permanently maintained. Negative pressure in the context of the field at issue here, relates to a negative pressure, which is typically between 0 and 250 mmHg (mm mercury column) below the surrounding atmospheric pressure. It has been shown that this facilitates wound healing. For the negative pressure tight sealing, a negative pressure bandage is provided, which for example can include a pressure tight—or negative pressure tight film layer, which is typically adhesively attached to an uninjured body region that surrounds the wound to achieve a tight sealing. In order to apply and maintain a negative pressure to the wound space by way of a negative pressure generating device, i.e., a vacuum pump in the broadest sense, conduits to which negative pressure can be applied can be used in the systems for negative pressure therapy at issue here, which conduits interact with the negative pressure bandage in order to apply negative pressure to or into the wound space.

DE 10 2009 060 596 A1 discloses a connection device of the aforementioned type. The conduit is attached to and fixed to the wound-averted side of the coupling body. For the negative pressure communication with the wound space, openings are provided which extend through the walling of the conduit and the coupling body. A similar connection device is known from DE 10 2010 006 272 A1 in which the conduit itself forms a coupling body in that a wound-side longitudinal end section of the conduit transitions on both sides one-piece into lateral wing sections. The one-piece configuration i.e., the production of conduit and coupling body in a single manufacturing step is extremely complicated however and therefore disadvantageous.

Further connection devices are known from DE 10 2010 006 273 A1. In this embodiment, the conduit is arranged sandwich-like between different layers, which form a coupling body toward the wound bandage and are sealingly fixed which is also cumbersome.

In WO 2009/124548 it is proposed to produce a rather cup-shaped or plate-shaped coupling body with radially extending contact areas and with a receiving section for inserting a conduit, one-piece in the injection molding method.

It would therefore be advantageous to provide an improved connection device which is reliable and can be manufactured economically and can be configured relatively flat.

SUMMARY OF THE INVENTION

According to one aspect of the present invention, a connection device for use in the negative pressure therapy of wounds includes a flexible conduit which can be impinged with negative pressure and/or fluid media, wherein the conduit has at least two lumens, a coupling body formed by an elastomeric flexible material which is non-detachably injection molded to a wound-side end section of the conduit, and is constructed for placement on a negative pressure bandage which covers and seals the wound negative pressure tight against the atmosphere, wherein the conduit communicates through at least one opening in the coupling body with the wound space, and an end cap attached and preferably non-detachably fastened to the injection molded-on material of the coupling body, thereby sealing the coupling body tight against the outside.

Preferably, the conduit of the connection device according to the invention is constructed flat and is initially manufactured separately, which has the general advantage of enabling an endless manufacturing, preferably by extrusion, wherein subsequent thereto sections of a respective desired line length can be generated by cutting. The coupling body is then formed by injection molding to an end section of the conduit and is finished by attaching and fastening of the end cap. Manufacturing the coupling body in this way has the particular advantage that a sealing transition to the conduit can be formed reliably or in other words, that when forming the coupling body the conduit is sealingly attached to the coupling body.

The at least one opening in the walling of the coupling body, which walling faces the negative pressure bandage, can either be manufactured during the injection molding process by suitable configuration of the injection molding tool or in a subsequent work step for example by a punching process. However, manufacturing the at least one opening by injection molding is preferred. Preferably, multiple openings are provided, which are preferably configured as oblong holes.

According to another advantageous feature of the invention, the conduit leads to the coupling body essentially parallel to the plane of the two-dimensional extent of the coupling body. In this context, "essentially parallel" means a slant of up to 15° in relation to this plane of extent, which also forms the contact surface to the negative pressure bandage.

According to another advantageous feature of the invention, the coupling body can be configured so that after being injection molded-on, at least one lumen ends freely and that by fastening the end cap the freely ending lumen is sealed tight to the outside. In this variant it is advantageous that during the injection molding of the elastomeric material that forms the coupling body onto the end section of the conduit, fluid conducting sections which in the following are referred to as lumens, are formed inside the coupling body. From a process point of view this is realized for example by providing rod-shaped elements in the injection molding tool which form these lumens and in particular prevent that during the injection molding process, material enters the lumens of the conduit. It is also conceivable however that the conduit or the end section of the conduit extends up to the inner side of the end cap and its lumens are then sealed closed by the end cap.

According to another advantageous feature of the invention, the coupling body can be configured so that after the injection molding-on at least two lumens end freely and by fastening the end cap the freely ending lumens are fluidly connected to each other and are sealed tight against the outside by way of the fact that the end cap has a recess which connects the at least two lumens to each other. This has the advantage that the lumens of the conduit or the coupling body are connected at their distal ends and with this quasi without dead space.

This is particularly advantageous when one of the lumens is to serve as rinsing lumen, because in this case a complete rinsing of the lumens can be ensured without deposits forming at sites of dead spaces which cannot or only with difficulties be reached by flow. The formation of this communication at the distal ends of the lumens by fastening and sealing the end cap is a very economical way for producing the coupling body or the connection device. The end cap itself can be produced in an injection molding process.

According to another advantageous feature of the invention, the conduit and the coupling body and preferably also the end cap can be formed from a flexible elastomeric material, in particular from silicone or on silicone basis which has a Shore-A hardness of at most 65, in particular of at most 60, in particular of at most 50, in particular of at most 40, and further of at least 10 in particular of at least 15.

According to another advantageous feature of the invention, the end cap can be materially connected, in particular and preferably glued, to the injection molded material of the coupling bod. Preferably, the end cap closes the coupling body in a rounded manner. A transition to the end cap is preferably essentially free of grooves and steps.

For perfecting the joining of the end cap, the coupling body can have a preferably thin border region in which the end cap is inserted and which surrounds the end cap collar-like. Such a border region, which for example has a wall thickness of 0.2 to 1.5 mm, can be very easily produced by the injection molding process because it only has to protrude by a few millimeters, for example 1 to 10 mm, in particular 1 to 8 mm, in particular 1 to 5 mm, in order to form a collar-like receptacle for the end cap.

According to another advantageous feature of the invention, the coupling body can be configured with a first region, which includes a first part that at least partially surrounds the end section of the conduit, an intermediate part adjoining the first part, and the end cap, and with a second region, which has a smaller thickness relative to the first region and extends two-dimensionally. The mentioned intermediate part of the coupling body results when the end section of the conduit does not essentially extend over the entire longitudinal extent of the first region, but only forms a relatively short edge for injection molding-on the coupling body. In this case the lumens of the conduit continue into the interior of the coupling body by channel-forming recesses i.e., by lumens which are formed during the injection molding. A configuration of the coupling body with a relatively short portion, which surrounds the end section of the conduit and an adjoining intermediate part in which the lumens of the conduit are continued, is preferred. In this case it is advantageous when the end section of the conduit, i.e., the region of the conduit that is surrounded with material of the coupling body, extends into the coupling body by about 2 to 15 mm and further in particular 3 to 12 mm, and further in particular 5 to 10 mm.

According to another advantageous feature of the invention, the aforementioned two-dimensionally extending second region of the coupling body can have a thickness of 0.1 to 2 mm, in particular 0.1 to 1.5 mm, in particular 0.1-1.0 mm, in particular 0.1-0.8 mm, in particular 0.1-0.5 mm.

According to another advantageous feature of the invention, the two-dimensionally extending second region can have an extent so that a contact surface of the second region with the wound-averted top side of the negative pressure bandage is at least 1.5 times, in particular at least 1.8 times the size of the contact surface of the first region. The contact surface is calculated or viewed in the perpendicular projection onto the plane of extent of the coupling body.

According to another advantageous feature of the invention, the first region of the coupling body can extend the longitudinal extent of the conduit, and the second region of the coupling body can flank the first region on both sides of its longitudinal extent and when viewed from the top has a butterfly-like shape, i.e., has a constriction on both sides of the longitudinal extent.

According to another advantageous feature of the invention, the maximal thickness of the first region of the coupling body which is injection molded to the conduit can be at most 3 mm, in particular at most 2 mm greater than the thickness of the conduit, and the width of the first region of the coupling body can be at most 5 mm, in particular at most 3 mm, in particular at most 2 mm greater than the width of the conduit.

According to another advantageous feature of the invention, the extent of the thickness of the conduit can be at most 7 mm, in particular at most 6 mm, in particular at least 3 mm and further 4-6 mm, wherein its width transverse to the longitudinal extent can be at least 12 mm, in particular at least 15 mm, in particular between 15 mm and 30 mm, in particular between 15 mm and 25 mm, in particular between 15 mm and 22 mm.

When the conduit is configured multi-lumen, it can be advantageous when one lumen is configured significantly greater than the other lumens. The lumen which is configured to have a greater conducting cross section is suited in this case as suction lumen which can be impinged with negative pressure for discharging wound secretes and particulate matter which is often contained therein. The other lumens which are configured with the smaller conducting cross section are suited as rinsing lumens or for delivering fluid media which are in particular charged with active agents.

In order to prevent collapsing of an in particular flat conduit it can be advantageous to provide supporting means inside a lumen, which supporting means preferably extend one-piece from the inner walls of the conduit and thereby define or delimit partial cross sections of a lumen. In this case it can also be advantageous that two lumens or partial sections of a lumen inside the conduit, which are not separated from each other in a negative pressure tight manner, are sealed pressure tight against each other in their extension inside the coupling body and transverse to their longitudinal extent. Thus, according to this further inventive idea lumens are formed inside the coupling body, which are separated from each other, which however at the same time can be fluidly connected at their distal ends if this is considered as useful. This increases the stability of the coupling body and effectively prevents collapsing.

According to another advantageous feature of the invention, the coupling body can be configured with three lumens that extend adjacent one another and which are fluidly connected at their ends, wherein one lumen is configured a rinsing lumen and the two other lumens are configured as suction lumens. It can further be especially advantageous when the lumen that is configured as rinsing lumen is closed in the direction toward the wound i.e., without openings and then preferably only communicates via its distal end with the further lumens inside the coupling body. In a refinement of the invention, this can—as mentioned before—advantageously be realized by a flow communication via the end cap.

For connecting the connection device to the negative pressure bandage it is advantageous that a side of the coupling body which side faces the negative pressure bandage is configured with an adhesive layer or with an adhesive coating in order to create a connection to the negative pressure bandage which is essentially negative pressure tight against the environment.

According to another advantageous feature of the invention, the adhesive layer or coating can be formed by an at least three-layered adhesion-providing layer, which includes a center carrier layer, a first adhesive layer which is held on the carrier layer and faces the coupling body and a second adhesive layer which is held on the carrier layer and faces away from the coupling body. The adhesion-providing layer is configured so as to not block the at least one opening in the coupling body and so that the first adhesive layer and the second adhesive layer are formed by different adhesive materials with different adhesive properties. In the case when the coupling body is formed from silicone, it is advantageous that the first adhesive layer includes a silicone glue. It is further advantageous when the second adhesive layer includes an acrylate glue which is generally suited to enter into an essentially negative pressure tight connection with typical wound bandage materials. Preferably, the first and second adhesive layers have a thickness of 20 to 400 µm. In the center carrier layer, a nonwoven, a flat material with a textile bonding, such as for example a knitted or woven fabric, or a plastic foil, a metal foil or a composite material made thereof is preferred. It is further advantageous when the wound-facing side of the second adhesive layer is covered by a detachable protective layer, which is preferably configured two-part and is further preferably provided with a graspable region that protrudes over the second adhesive layer.

According to another advantageous feature of the invention, a connection piece preferably made of a flexible polymeric material is fastened to the wound-averted end of the conduit, i.e. the end of the conduit which faces a negative pressure generating device, preferably in a negative pressure tight manner and preferably materially bonding in particular by an adhesive connection. This connection piece can either serve for connection with a further conduit section or it serves as connecting member to a further coupling element in particular a quick coupling element or plug-in connector.

The aforementioned connection piece is preferably made of a flexible polymeric material whereby a closure member is formed which is safely held thereon one-piece. This closure member can have one or more closure plug sections and can close openings of the connection piece or of a quick coupling element which can be detachably arranged on the connection part by interference fit. The connection device includes advantageously such a quick coupling element made of bending stiff material, in particular made of thermoset material, which is connected or connectable to the connection piece by interference fit.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

The Figures show a connection device according to the invention overall designated with the reference numeral 2 for use in the negative pressure therapy of wounds. For this, the connection device 2 is connectable with a not shown negative pressure generating device which typically acts in cooperation with a liquid-collecting container for discharging and collecting wound secretes that are suctioned out of the wound space and rinsing media. The connection device serves for negative pressure tight coupling to a negative pressure bandage which again seals the wound essentially negative pressure tight against the environment, wherein a negative pressure communication to the wound space is established.

The connection device 2 according to the invention includes a conduit overall designated with the reference numeral 4 and a coupling body 6. The coupling body 6 is injection molded to a wound-side end section 8 of the conduit in a plastic injection molding process.

On a wound-averted end 10 of the conduit 4 for example a connection piece 12 and a quick coupling element 14 for further connection in the direction of the not shown negative pressure device is provided.

The coupling body 6 includes a first region 16 which in the exemplary shown case is block-shaped, and continues the longitudinal extent of the conduit 4, and a second region 18 which has a significantly smaller thickness than the first region and extends two-dimensionally, which second region starting from the first region 16 extends away preferably on both sides and further preferably on at least three sides of the first region 16 so that a large contact surface of the coupling body 6 to a not shown negative pressure bandage can be realized.

The first region 16 of the coupling body 6 includes a part 20, which at least partially surrounds the end section 8 of the conduit 4, an intermediate part 24 which adjoins the part 20 in a longitudinal direction 22 and an end cap 26. The part 20 which surrounds the end section, the intermediate part 24 and the two-dimensionally extending second region 18 of the coupling body 6 are produced one-piece from a flexible elastomeric material preferably from silicone or on silicone basis. For this, the conduit 4 or the wound-side end section 8 of the conduit 4 is introduced into a not shown injection mold and the elastomeric material which forms the coupling body 6 is injection molded to the end section 8 of the conduit 4. The injection mold is configured or equipped so that flow channel-forming lumens 28, 30 of the conduit are continued inside the coupling body 6. Thus, corresponding hollow space or channel-forming means have to be provided inside the injection molding tool in particular in the form of rods or the like. Even though not shown, it is also conceivable that conduit 4 or its end section 8 extend as far as to the end cap 26. In this case, the part 20, which at least partially surrounds the end section 8 of the conduit 4 would be configured longer and the intermediate part 24 would not be required or would be configured much shorter. It has been proven advantageous when the conduit 4 protrudes into the coupling body 6 only with a relatively short end section 8 because in this case the freedom of design of the coupling body 6 inside the intermediate part 24 is greater and openings 32 in a walling 34 of the coupling body 6 which walling 34 faces the negative pressure bandage can be formed already during the injection molding process.

The intermediate part 24 is thus formed with lumens 36, 38, 40 in its interior which are separated from each other transverse to the longitudinal direction 22, and as can be seen from the Figures, adjoin the lumens 28, 30 of the conduit 4. In the shown example the lumen 30 of the conduit 4 is configured with a much greater cross-section than the lumen 28; it includes so to speak two partial cross sections, which are designated with the reference signs 30a, and 30b, which however are not fluidly separated from each other. They are delimited by longitudinal ribs 41 in the interior of the conduit 4, which longitudinal ribs 41 prevent a collapsing of the lumen 30. The lumens 38 and 40 which adjoin the lumen 30 or the partial cross sections 30a, 30b of the conduit inside the intermediate part 24 of the coupling body 6 however are separated from each other by a wall 42 which is formed from the material of the intermediate part 24 (which can be best seen from FIGS. 4 and 5). This separated configuration is preferred, however not strictly required. It has the advantage that thereby the stability of the coupling body 6 against collapsing of its lumens 36, 38, 40 is increased and it's rinsability with rinsing media is improved.

Figure 4:
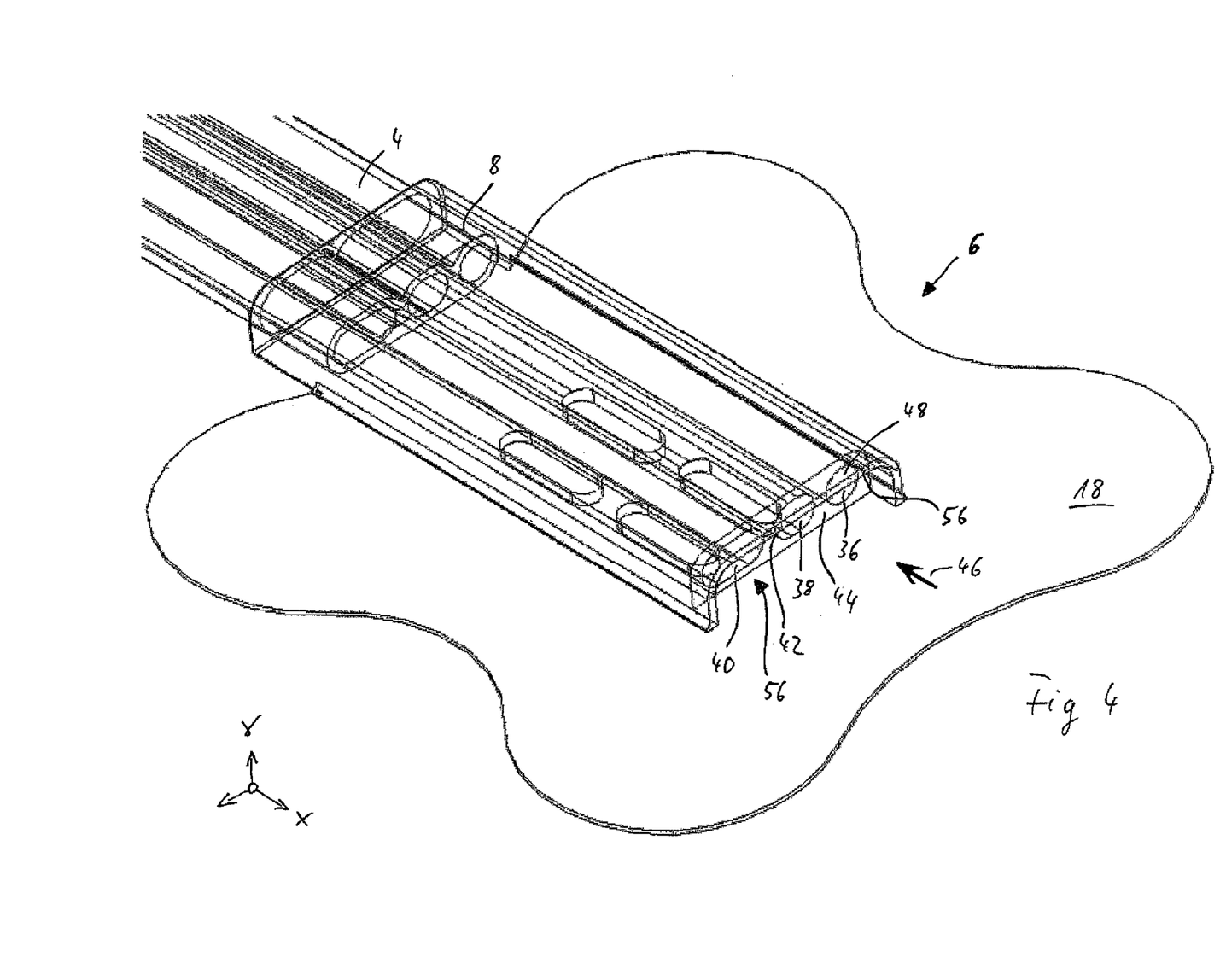
FIG. 4 shows a perspective view according to FIG. 3 however without end cap.
Figure 5:
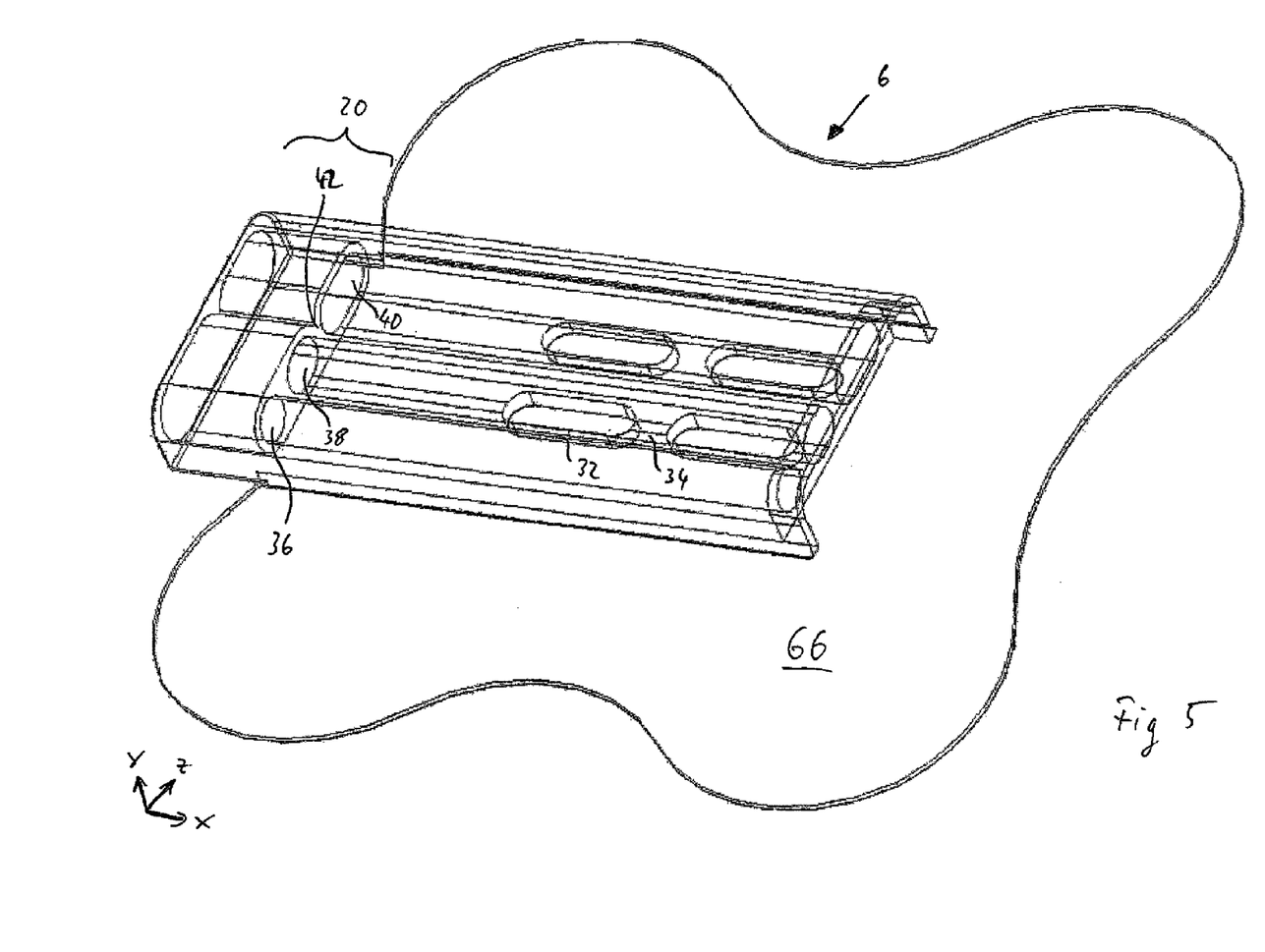
FIG. 5 shows a perspective view of the connection device in the direction toward the wound facing side of the connection device however without conduit and without end cap.

FIG. 4 shows the conduit 4 with the injection molded-on i.e., one-piece coupling body 6 after the injection molding process i.e., still without end cap 26. FIG. 5 shows the coupling body 6 again without end cap 26 and without conduit 4 i.e., in a state which does not exist per se for illustrating the part 20 of the coupling body, which part 20 surrounds the end section 8 of the conduit 4.

It can further be best seen from FIG. 4 that the lumens 36, 38, 40 of the coupling body end freely at a front side 44 of the intermediate part 24 which front side 44 faces the end cap 26. They are sealed negative pressure tight against the environment by attaching and negative pressure tight fastening of the end cap 26. The end cap 26 which is fastened by interference fit or is preferably non-detachably materially connected in particular by means of glue, completes the body 6 of the connection device according to the invention 2. As can further be best seen from FIG. 4, a border region 48 is formed during injection molding-on the elastomeric material which forms the coupling body 6, which border region 48 extends opposite to an attachment direction 46 in which the end cap 26 is attached and which is preferably relatively thin for example only 0.5 to 1.5 mm thick and delimits a receiving opening 50 for the end cap 26. In the exemplary show case the border region 48 extends over three sites so that the receiving opening 50 is delimited on the fourth side from the two dimensionally extending second region 18 of the coupling body 6.

Figure 6:
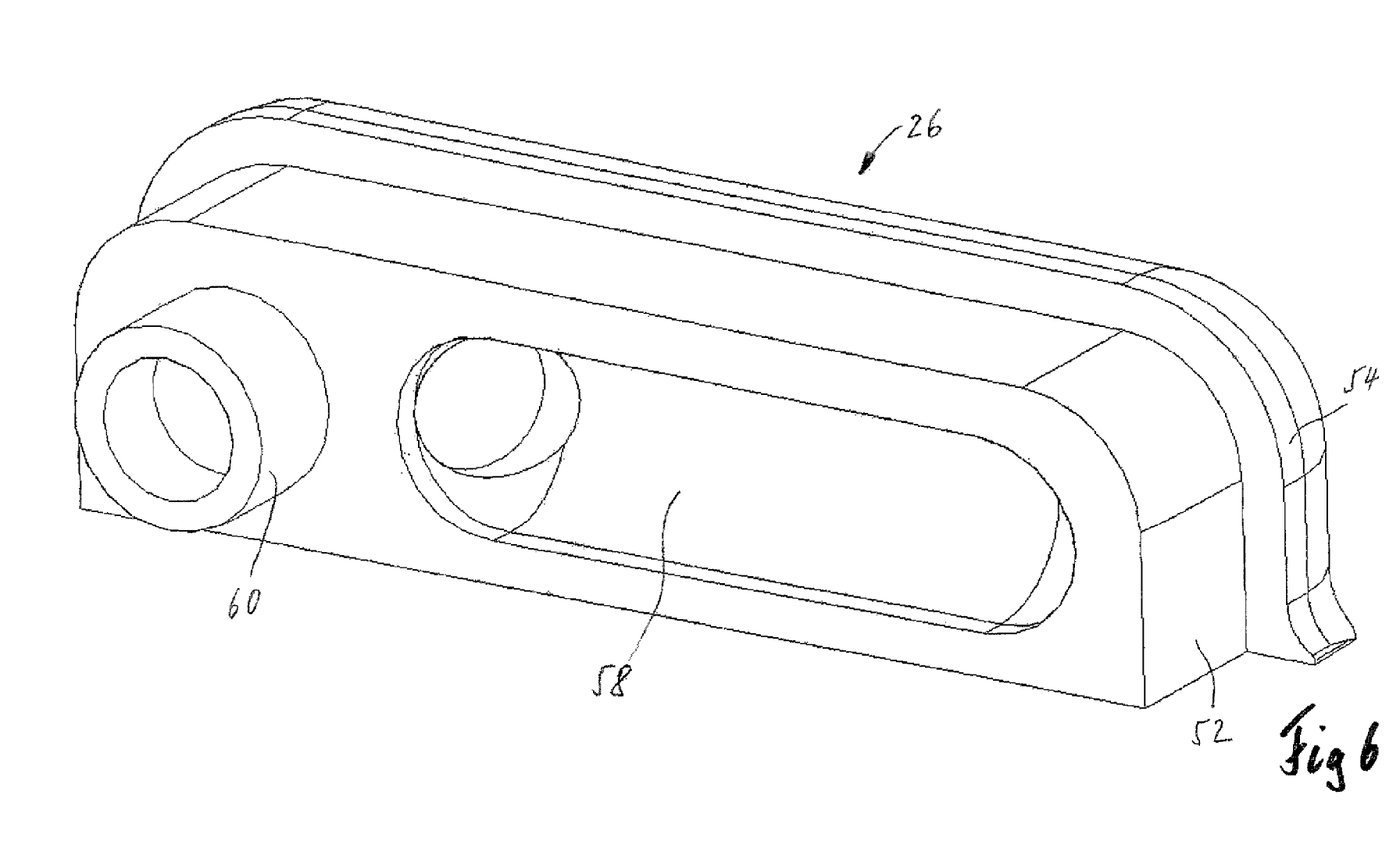
FIG. 6 shows a perspective view of the end cap.

The end cap 26, which is preferably made from the same material as the coupling body 6 is shown in FIG. 6 in a perspective view. An engagement section 52 can be recognized with which the end cap 26 engages in the receiving opening 50, and a section 54 which is visible from the outside and which completes the coupling body 6 visibly towards the outside. The end cap 26 is preferably but not necessarily configured so that the visible section 54 protrudes relative to the engagement section 52 just by the thickness of the protruding border region 48 of the intermediate part 24. In this way the end cap 26 abuts the front side 56 of the border region 48. This results in a further labyrinth-like sealing and in addition a gap-free step-free transition from the intermediate part 24 to the end cap 26 can be realized.

The end cap 26 is further configured with a recess designated with the reference sign 58, by means of which a flow communication between at least two, in the exemplary showcase between three, lumens 36, 38, 40 is achieved i.e., starting from their distally ending openings in the region of the front site 44. The recess 58 can be realized in many different ways; in the simplest case for example in the form of an oblong hole shaped indentation that then adjoins the front site 44 of the intermediate part 24. In the exemplary concrete shown case, the end cap is configured with a tubular attachment 16 which when attaching the end cap 26 sealingly engages in the lumen 36 in the intermediate part 24, which is configured complementary to the tubular attachment 60. In the interior of the end cap 26, this tubular attachment leads into the transverse extending recess 58 which opens to the front side 44 of the intermediate part 24 in the form of an oblong hole. In this way a flow communication between all lumens 36, 38, 40 is established.

In the exemplary shown case it is advantageous that the lumen 28 of the conduit 4 and the lumen 36 adjoining the lumen 28 are configured as rinsing lumens inside the coupling body for delivering a fluid medium in the direction towards the wound. In this way, rinsing liquid or other fluids in particular air are conducted to the distal end openings of the lumens 38, 40 in the front side 44 in the intermediate part 24. This enables a dead-space free rinsing of the lumens; there is therefore no line section which is not immediately exposed to the flow along the flow path, which is considered particularly beneficial with regard to the intended functioning of the connection device and the negative pressure wound therapy performed therewith and with regard to reducing bacterial growth and infections. The end cap 26 therefore has a dual function i.e., on the one hand it completes the coupling body 6 and closes the openings of the lumens 36, 38, 40 which after the injection molding process open to the outside and on the other hand a flow communication between the lumens 36, 38, 40 is realized by the end cap 26.

For flow communication with the wound space, the already mentioned openings 32 in the wall 34 of the coupling body 6 which wall 34 faces the negative pressure wound bandage are formed. It can be seen from the Figures that the lumen 36 of the coupling body 6 which lumen functions as rinsing lumen does not have such an opening which is preferred but not strictly required. The openings 32 which are provided in the region of the longitudinal extent of the lumens 38, 40 are preferably formed as oblong holes and have a preferred length of 8 to 12 mm. In the exemplary shown case, two such oblong hole shaped openings are formed along the extent of each lumen 38, 40. During use, the lumens 38, 40 of the coupling body communicate via these openings 22 and via at least one opening in the negative pressure bandage with the wound space. Typically, the lumens 38, 40 of the coupling body 6 are impinged with negative pressure via the lumen 30 in the conduit 4; the lumens 38, 40 thus typically function as suction lumens for applying negative pressure and for discharging wound secrete, rinsing liquid or other supplied fluid media.

In the following, the shape of the two-dimensionally extending second region 18 of the coupling body 6 is described which shape is exemplary shown in the Figures. When viewed from the top, this shape or form can best be described as butterfly shape because this second region 18 when viewed in the longitudinal direction 22 has a constriction 62 on both sides. In this way, the dimensions of the coupling body 6 or its second region 18 are greater along outlined diagonals 64 which form an angle of about 45° to the longitudinal direction to 22, than in the longitudinal direction 22 and perpendicular thereto. In the exemplary and preferred shown case, the two-dimensionally extending second region 18 extends towards three sides past the also flat, however block-shaped first region 16 of the coupling body 6. In this way a very good connection to a not shown negative pressure bandage can be achieved because the occurring forces are evenly distributed over a large surface and can therefore be introduced into the regions of the wound-bandage which surround the wound and the body surface of the patients without local force peaks.

For connection to the negative pressure bandage, the coupling body includes a not shown adhesive layer on its side 66, which faces the negative pressure bandage. This adhesive layer is preferably formed as an at least three-layered adhesive providing layer, which has a center carrier layer, a first adhesive layer which is held on the carrier layer and faces the coupling body, and a second adhesive layer which is held on the carrier layer and faces away form the coupling body. The adhesive layers are each optimized with regard to forming an adhesive connection with the material of the coupling body or with the material of the negative pressure bandage. Regarding further features of this at least three layered adhesive providing layer reference is made to the not published DE 10 2011 108 726.9 whose subject matter is incorporated into the present application by reference.

Figures 1, 2:
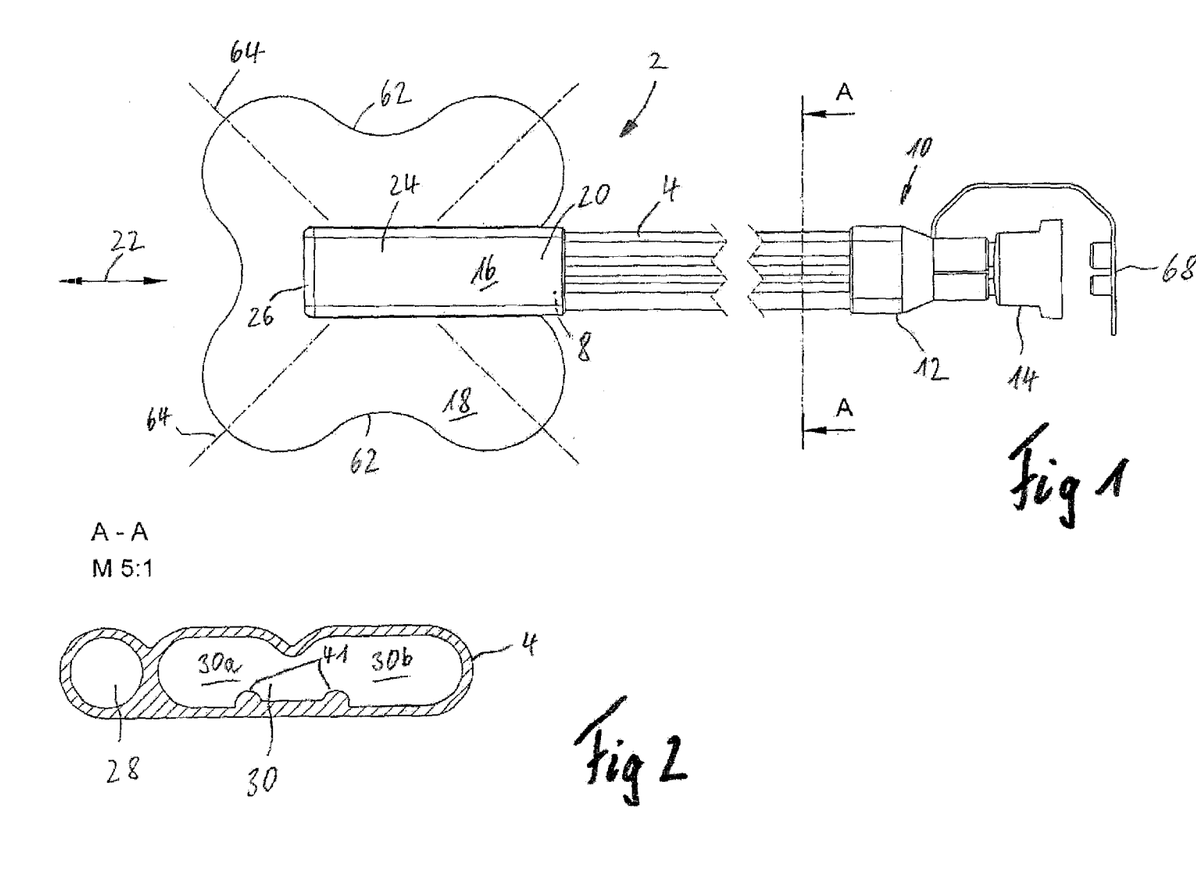
FIG. 1 shows a top view on a connection device according to the invention for use in the negative pressure therapy of wounds fur further connection with a not shown negative pressure generating device.
FIG. 2 shows a cross section through a conduit of the connection device according to FIG. 1.
Figure 3:
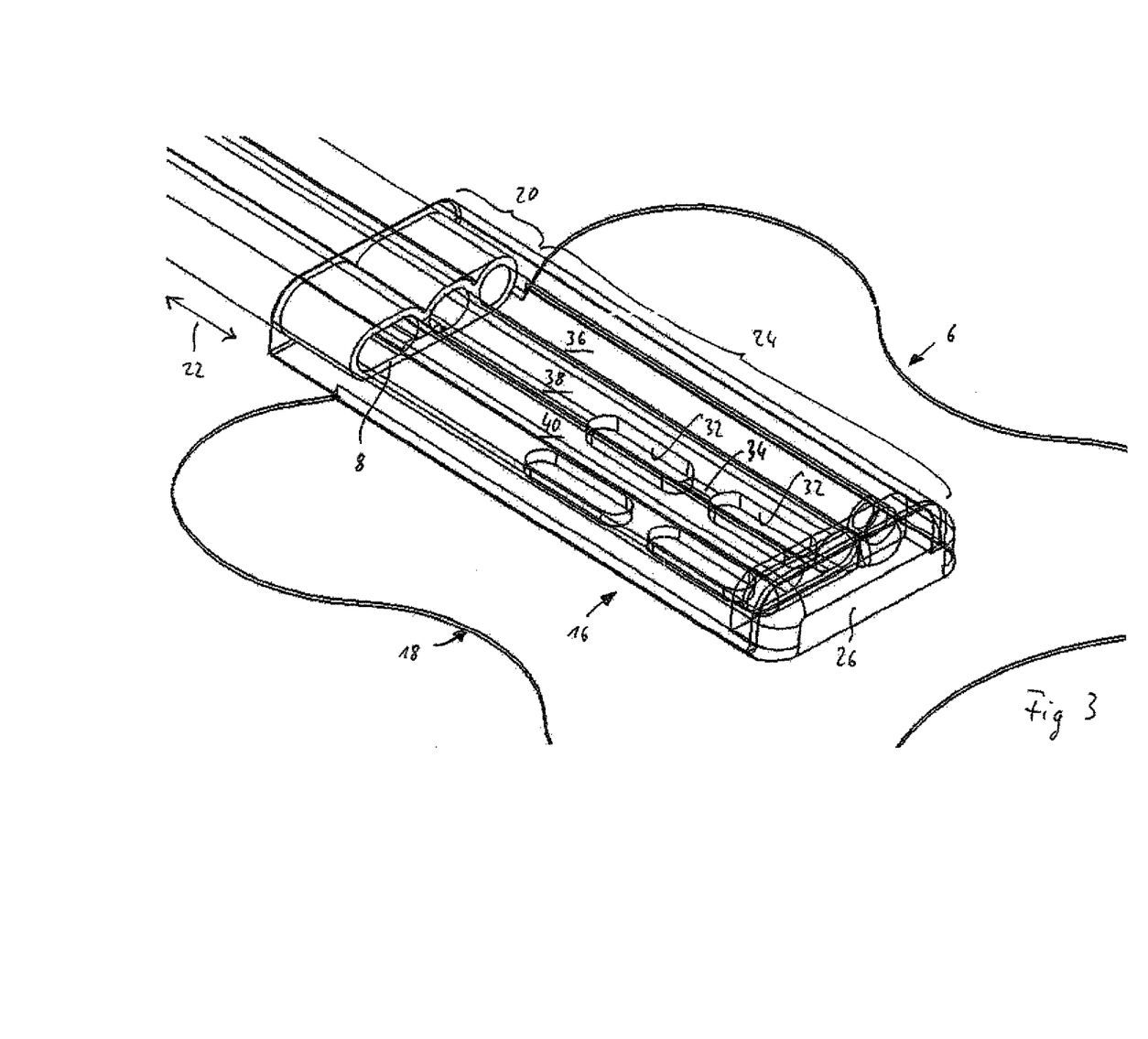
FIG. 3 shows an enlarged perspective partial view of the connection device according of FIG. 1 with view on the wound averted side of the connection device.

Finally, FIG. 1 shows the connection piece 12 at the wound-averted end 10 of the conduit, which connection piece 12 is preferably made of a flexible polymeric material and is that attached to the wound-averted end 10 of the conduit 4 in a negative pressure tight and preferably materially bonding manner. The connection piece 12 includes a closure member 68 which preferably adjoins the connection piece 12 one-piece and is therefore securely held on the connection piece 12, which closure member 68 is capable to close openings of the connection piece 12 or of a quick coupling element 14 which can be detachably arranged on the connection piece 12 in an interference fit. The connection piece is preferably an injection molded part which is produced one-piece together with the closure member 68. A further conduit section which leads to the not shown negative pressure generating device and the liquid collection container can be connected negative pressure tight to the quick-coupling element 14 via a complementary configured quick-coupling element While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. A connection device for use in the negative pressure therapy of wounds comprising:
   a flexible conduit which can be impinged with negative pressure and/or fluid media, said conduit having at least two lumens;
   a coupling body formed by an elastomeric flexible material which is non-detachably injection molded to a wound-side end section of the conduit, and being constructed for placement on a negative pressure bandage which covers and seals the wound negative pressure tight against the atmosphere, said conduit communicating with the wound space through at least one opening provided only on a wound-facing side of the coupling body; and
   an end cap attached to the injection molded-on material of the coupling body, thereby sealing the coupling body tight against the outside when the wound-facing side of the coupling body is placed on the negative pressure bandage, said end cap having a recess which fluidly connects the at least two lumens with each other.

2. The connection device of claim 1, wherein the conduit leads to the coupling body essentially parallel to a plane of a two-dimensional extent of the coupling body.

3. The connection device of claim 1, wherein the coupling body is configured so that after an injection molding-on, at least one lumen ends freely and that the freely ending lumen is sealed tight towards the out side by the fastened end cap.

4. The connection device of claim 1, wherein the conduit and the coupling body are formed from a flexible elastomeric material, said material having a Shore-A hardness of at most 65 and at least 10.

5. The connection device of claim 1, wherein the end cap is connected with the injection molded material of the coupling body.

6. The connection device of claim 1, wherein the end cap closes the coupling body in a rounded manner.

7. The connection device of claim 1, wherein the coupling body has a border region in which the end cap is inserted and which surrounds the end cap collar like in a circumferential direction.

8. The connection device of claim 1, wherein the coupling body has a first region and a second region, said first region including a first part which at least partially surrounds the end section of the conduit, an intermediate part which adjoins the first part, and the end cap, said second region having a smaller thickness relative to the first region and extending two-dimensionally.

9. The connection device of claim 1, wherein the end section of the conduit extends into the coupling body by about 2 to 20 mm.

10. The connection device of claim 8, wherein the second region of the coupling body is configured with a thickness of 0.1 -2.0 mm.

11. The connection device of claim 8, wherein the two-dimensional extent of the second region is configured so that a contact surface with which the second region contacts a wound-averted top side of the negative pressure bandage is at least 1.5 times as great as the contact surface of the first region.

12. The connection device of claim 8, wherein the first region of the coupling body continues a longitudinal extent of the conduit and the second region of the coupling body flanks the first region on both sides of a longitudinal extent of the first region and is formed in the shape of a butterfly when viewed from the top.

13. The connection device of claim 8, wherein a maximum thickness of the first region of the coupling body which is injection molded to the conduit is greater than the thickness of the conduit by at most 3 mm, and a width of the first region of the coupling body is greater than the width of the conduit by at most 5 mm.

14. The connection device of claim 1, wherein a thickness extent of the conduit is at most 7 mm, wherein a width of the conduit transverse to the longitudinal extent of the conduit is at least 12 mm.

15. The connection device of claim 1, wherein a first lumen of the at least two lumens of the conduit forms a rinsing lumen or a delivery lumen for fluid media to the wound and a second one of the at least two lumens of the conduit is constructed as suction lumen capable of being impinged with negative pressure for discharge of fluid media from the wound in a direction toward a negative pressure generating device, and wherein the second lumen has a greater cross-section than the first lumen.

16. The connection device of claim 1, wherein two of the at least two lumens or partial cross sections of one of the at least two lumens are not separated from each other in a negative pressure tight manner inside the conduit and are sealed pressure tight against each other transverse to their longitudinal extent upon continuing inside the coupling body.

17. The connection device of claim 1, wherein the coupling body includes three adjacently extending lumens which are fluidly connected at their ends, wherein one of the three lumens is configured as rinsing lumen and the remaining two of the three lumens are configured as suction lumens.

18. The connection device of claim 17, wherein the lumen which is configured as rinsing lumen is closed in the direction towards the wound and is fluidly collected with the remaining two of the three lumens only via its distal end.

19. The connection device of claim 18, wherein the rinsing lumen is fluidly connected with the remaining two of the three lumens only via the end cap.

20. The connection device of claim 1, wherein a side of the coupling body which side faces the negative pressure bandage is configured with an adhesive layer or an adhesive coating, for establishing a negative pressure tight adhesive connection to the negative pressure bandage.

21. The connection device of claim 1, wherein the adhesive layer or coating is formed by an at least three-layered adhesion-providing layer, having a center carrier layer, a first adhesive layer which is held on the carrier layer and faces the coupling body and a second adhesive layer which is held on the carrier layer and faces away from the coupling body, said adhesion providing layer being configured so that the at least one opening in the coupling body is not blocked and that the first adhesive layer and the second adhesive layer are formed from different adhesive materials with different adhesive properties.

22. The connection device of claim 21, wherein the coupling body is made from silicone and the first adhesive layer includes a silicon glue and/or wherein the second adhesive layer includes an acrylate glue.

23. The connection device of claim 21, further comprising a connection piece fastened on a wound-averted end of the conduit in a negative pressure tight.

24. The connection device of claim 23, wherein the connection piece further comprises a closure member which is securely attached to the connection piece and adjoins the connection piece in one-piece, said closure member being constructed to close openings of the connection piece or a quick coupling element by interference fit and detachably.

25. Connection device according to claim 23, further comprising a quick coupling element which is made of a bending stiff material, which is connected or capable of being connected with the connection piece by interference fit.

* * * * *

UNITED STATES PATENT AND TRADEMARK OFFICE
CERTIFICATE OF CORRECTION

PATENT NO.        : 9,586,000 B2
APPLICATION NO.   : 13/962713
DATED             : March 7, 2017
INVENTOR(S)       : Axel Eckstein et al.

Page 1 of 1

It is certified that error appears in the above-identified patent and that said Letters Patent is hereby corrected as shown below:

On the Title Page

With regard to the city of residence of the fourth inventor Oded Stein, replace "Kfar-Kama" with -- Kfar-Hahoresch --.

Page 2, in Line 4 of the foreign patent documents listed, replace "DE 2011009241" with -- DE 102011009241 --.

In the Claims

In Column 12, Claim 18, Line 9 replace "collected" with -- connected --.

In Column 12, Claim 23, Line 36 after "negative pressure tight" insert -- manner --.

Signed and Sealed this
Sixteenth Day of May, 2017

Michelle K. Lee
*Director of the United States Patent and Trademark Office*